US008946463B2

(12) United States Patent
Klasovsky et al.

(10) Patent No.: US 8,946,463 B2
(45) Date of Patent: *Feb. 3, 2015

(54) PROCESS FOR THE DIRECT AMINATION OF ALCOHOLS USING AMMONIA TO FORM PRIMARY AMINES BY MEANS OF A XANTPHOS CATALYST SYSTEM

(75) Inventors: Florian Klasovsky, Haltern am See (DE); Thomas Tacke, Alzenau (DE); Jan Christoph Pfeffer, Hanau (DE); Thomas Haas, Muenster (DE); Matthias Beller, Nienhagen (DE); Andreas Martin, Berlin (DE); Jens Deutsch, Rangsdorf (DE); Angela Koeckritz, Berlin (DE); Sebastian Imm, Langenselbold (DE); Juergen Haberland, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/000,400

(22) PCT Filed: Dec. 14, 2011

(86) PCT No.: PCT/EP2011/072771
§ 371 (c)(1),
(2), (4) Date: Aug. 20, 2013

(87) PCT Pub. No.: WO2012/113475
PCT Pub. Date: Aug. 30, 2012

(65) Prior Publication Data
US 2013/0331580 A1 Dec. 12, 2013

(30) Foreign Application Priority Data

Feb. 21, 2011 (DE) .......................... 10 2011 004 472

(51) Int. Cl.
*C07D 213/38* (2006.01)
*C07C 213/02* (2006.01)
*C07C 227/06* (2006.01)
*C07D 493/04* (2006.01)
*C07C 209/16* (2006.01)
*C07C 227/08* (2006.01)

(52) U.S. Cl.
CPC ............. *C07C 209/16* (2013.01); *C07C 213/02* (2013.01); *C07C 227/08* (2013.01); *C07D 213/38* (2013.01); *C07C 227/06* (2013.01); *C07D 493/04* (2013.01); *C07C 2101/14* (2013.01); *C07C 2103/74* (2013.01)
USPC ........... 556/136; 546/329; 564/402; 564/480; 564/447; 549/464; 560/125; 554/114; 514/185

(58) Field of Classification Search
USPC .......................................... 514/185; 556/136
See application file for complete search history.

(56) References Cited

U.S. PATENT DOCUMENTS

| 7,148,176 B2 | 12/2006 | Beller et al. |
|---|---|---|
| 7,758,897 B2 | 7/2010 | Roettger et al. |
| 8,372,595 B2 | 2/2013 | Schaffer et al. |
| 8,378,127 B2 | 2/2013 | Dingerdissen et al. |
| 8,604,227 B2 | 12/2013 | Petrat et al. |
| 2001/0047097 A1 | 11/2001 | Trauthwein et al. |
| 2002/0087036 A1 | 7/2002 | Haas et al. |
| 2007/0207501 A1 | 9/2007 | Wolf et al. |
| 2010/0068773 A1 | 3/2010 | Marx et al. |
| 2010/0190224 A1 | 7/2010 | Poetter et al. |
| 2010/0261237 A1 | 10/2010 | Verseck et al. |
| 2010/0291644 A1 | 11/2010 | Marx et al. |
| 2010/0324257 A1 | 12/2010 | Karau et al. |
| 2011/0039313 A1 | 2/2011 | Verseck et al. |
| 2011/0039977 A1 | 2/2011 | Schuetz et al. |
| 2011/0118433 A1 | 5/2011 | Pötter et al. |
| 2011/0118504 A1 | 5/2011 | Haas et al. |
| 2011/0171702 A1 | 7/2011 | Reinecke et al. |
| 2011/0189742 A1 | 8/2011 | Haas et al. |
| 2011/0251399 A1 | 10/2011 | Dingerdissen et al. |
| 2011/0257429 A1 | 10/2011 | Schraven et al. |
| 2012/0034665 A1 | 2/2012 | Haas et al. |
| 2012/0041216 A1 | 2/2012 | Sieber et al. |
| 2012/0232292 A1* | 9/2012 | Schaub et al. ............... 549/492 |
| 2012/0232294 A1* | 9/2012 | Schaub et al. ............... 549/495 |
| 2012/0232309 A1* | 9/2012 | Schaub et al. ............... 564/474 |
| 2012/0245375 A1 | 9/2012 | Hannen et al. |
| 2012/0264182 A1 | 10/2012 | Reinecke et al. |
| 2013/0052700 A1 | 2/2013 | Poetter et al. |
| 2013/0092233 A1 | 4/2013 | Pawlik et al. |
| 2013/0130319 A1 | 5/2013 | Schaffer et al. |
| 2013/0165672 A1 | 6/2013 | Klasovsky et al. |
| 2013/0165685 A1 | 6/2013 | Hannen et al. |
| 2013/0183725 A1 | 7/2013 | Poetter et al. |
| 2013/0245276 A1* | 9/2013 | Klasovsky et al. ........... 546/329 |

FOREIGN PATENT DOCUMENTS

| WO | 98 54115 | 12/1998 |
|---|---|---|
| WO | 02 10178 | 2/2002 |

(Continued)

OTHER PUBLICATIONS

Hamid; Chem. Commun. 2007, 7, 725-727.*
Dorwald; Side Reactions in Organic Synthesis, 2005, Wiley: VCH, Weinheim, chapter 1.*
Das; Angew. Chem. Int. Ed. 2012, 51, 150-154.*
U.S. Appl. No. 14/126,607, filed Dec. 16, 2013, Haas, et al.
U.S. Appl. No. 14/110,450, filed Oct. 8, 2013, Klasovsky, et al.
U.S. Appl. No. 09/424,701, filed Jan. 25, 2002, Beller, et al.
U.S. Appl. No. 13/989,419, filed May 24, 2013, Klasovsky, et al.

(Continued)

*Primary Examiner* — John Mabry
*Assistant Examiner* — Daniel Carcanague
(74) *Attorney, Agent, or Firm* — Oblon, Spivak, McClelland, Maier & Neustadt, L.L.P.

(57) ABSTRACT

The present invention relates to a chemocatalytic liquid-phase process for the direct one-stage amination of alcohols to primary amines by means of ammonia in high yields using a catalyst system containing at least one transition metal compound and a xantphos ligand.

18 Claims, No Drawings

(56) References Cited

FOREIGN PATENT DOCUMENTS

| WO | 02 36260 | 5/2002 |
| --- | --- | --- |
| WO | 2004 052896 | 6/2004 |
| WO | 2009 146977 | 12/2009 |
| WO | 2010 089171 | 8/2010 |
| WO | 2010 089213 | 8/2010 |
| WO | 2012 031884 | 3/2012 |
| WO | 2012 076560 | 6/2012 |
| WO | 2012 113475 | 8/2012 |
| WO | 2012 171666 | 12/2012 |
| WO | 2013 020839 | 2/2013 |

OTHER PUBLICATIONS

Imm S. et al. "An Efficient and General Synthesis of Primary Amines by Ruthenium-Catalyzed Amination of Secondary alcohols with Ammonia" Angewandte Chemie, International Edition, vol. 49(44), pp. 8126-8129, XP002669003, (2010).

Imm S. et al. "Improved Ruthenium-Catalyzed Amination of Alcohols with Ammonia: Synthesis of Diamines and Amino Esters", Angewandte Chemie. Internation Edition, vol. 50, No. 33, pp. 7599-7603, XP002664616, (Jul. 2011).

International Search Report Issued Feb. 24, 2012 in PCT/EP11/72771 Filed Dec. 14, 2011.

U.S. Appl. No. 14/233,505, filed Jan. 17, 2014, Poetter, et al.
U.S. Appl. No. 14/237,121, filed Feb. 4, 2014, Haas, et al.
U.S. Appl. No. 14/238,591, filed Feb. 12, 2014, Schaffer, et al.
U.S. Appl. No. 14/238,576, filed Feb. 12, 2014, Schaffer, et al.
U.S. Appl. No. 14/363,178, filed Jun. 5, 2014, Haas, et al.
U.S. Appl. No. 14/363,165, filed Jun. 5, 2014, Pfeffer, et al.
U.S. Appl. No. 14/367,610, filed Jun. 20, 2014, Haas, et al.
U.S. Appl. No. 14/373,089, filed Jul. 18, 2014, Engel, et al.
U.S. Appl. No. 14/380,483, filed Aug. 22, 2014, Schiemann, et al.

\* cited by examiner

PROCESS FOR THE DIRECT AMINATION OF ALCOHOLS USING AMMONIA TO FORM PRIMARY AMINES BY MEANS OF A XANTPHOS CATALYST SYSTEM

The present invention relates to a chemocatalytic liquid-phase process for the direct one-stage amination of alcohols to primary amines by means of ammonia in high yields using a catalyst system containing at least one transition metal compound and a xantphos ligand.

PRIOR ART

The conversion of oxygen-containing functional groups into nitrogen-containing functional groups represents an essential transformation for the synthesis of many organic compounds. A series of classical methods for achieving the stated task are known in the literature and in industry. In the overwhelming majority of publications, a primary or secondary alcohol is reacted with a primary or secondary organic amine. The reaction of a primary or secondary alcohol with ammonia to form primary amines has, on the other hand, been described only for use of particular process conditions, catalysts and a few alcohols.

The challenge for all known processes is to achieve high selectivities to the primary amines since these are more nucleophilic than ammonia and can consequently react preferentially to form higher amines. While the conversion of an isolated hydroxyl function into an amino function is approximately thermally neutral, the formation of secondary and tertiary amines is exothermic at about 30 kJ/mol in each case and is therefore also thermodynamically preferred over the formation of primary amines.

Direct Amination in the Gas Phase

The single-stage direct conversion of a primary or secondary hydroxyl group by means of ammonia into a primary amine is in the case of lower, readily volatile alcohols restricted mainly to gas-phase reactions. Here, the appropriate alcohol is vaporized and reacted under suitable conditions (pressure, temperature, hydrogen partial pressure and if applicable inert gas partial pressure) over a predominantly heterogeneous catalyst. This procedure is described, for example, in the publications U.S. Pat. No. 4,314,084, U.S. Pat. No. 5,530,127, U.S. Pat. No. 5,932,769, FR 1347648, U.S. Pat. No. 3,270,059, U.S. Pat. No. 4,111,840, U.S. Pat. No. 4,123,462, DE 1667193, Fischer et al. (J. Catal., 1999, 182, 289-291) or Jenzer et al. (Catal. Lett., 1999, 61, 111-114).

A disadvantage of most heterogeneously catalysed gas-phase processes is the use of high temperatures (up to 400° C.) and pressures (up to 300 bar), as a consequence of which not only the desired primary amines but frequently also considerable amounts of higher amines, alkenes and alkanes are formed. In addition, corresponding to the characteristic pressure and temperature conditions of a gas-phase reaction, only substrates which can be vaporized and reacted without a loss can be converted in economical yields into amines by means of the processes mentioned, and only amines which can be condensed or resublimed without a loss can be prepared. Substrates or their corresponding amines, in particular those having a long carbon chain, which are subject to decomposition under such conditions are therefore reacted in liquid-phase syntheses in the literature and in industry.

Reductive Amination

Processes known to those skilled in the art for preparing primary amines from alcohols in the liquid phase by means of reductive amination utilize a multistage procedure which can be associated with a change in the oxidation state of the carbon atom bearing the hydroxyl group. A distinction can be made between these and processes which proceed to completion with retention of the oxidation stage (direct amination). Alcohols can classically be prepared with a change in the oxidation state of the carbon atom bearing the hydroxyl group (reductive amination) by oxidation to the corresponding carbonyl compound, subsequent formation of the imine by reaction with an amine component (primary, secondary amine or ammonia) and subsequent homogeneously or heterogeneously catalysed reduction of the imine by means of hydrogen. However, the two-stage procedure with isolation of the carbonyl compound is time-consuming and costly.

Specific Multistage Processes

Alcohols can be converted into amines with retention of the oxidation state of the carbon atom bearing the hydroxyl group (direct amination) by means of multistage substitution reactions. Apart from the financial and time outlay for isolation of the intermediates, disadvantages of corresponding processes are, in particular, the handling of the explosive and toxic azides which are frequently employed here and the formation of stoichiometric amounts of coproducts.

Direct Liquid-Phase Amination of Alcohols

The direct single-stage liquid-phase amination of alcohols by means of ammonia has been described for some time in the scientific and patent literature. In some cases, the processes described cannot be unambiguously classified as gas-phase or liquid-phase processes because of the process conditions employed.

According to DE 19507007, ethanolamine can be aminated to ethylenediamine over oxide-supported ruthenium catalysts at temperatures of about 170° C. and a pressure of 200 bar, but the achievable yields remain below 40% and no other examples have been described.

The preparation of monovalent, optionally functionalized primary amines in high yields from the corresponding monovalent, optionally functionalized primary alcohols is described in the studies by Milstein et al. (Angew. Chem. Int. Ed., 2008, 47, 8661-8664). Here, the direct single-stage amination of primary aliphatic and benzylic alcohols, sometimes substituted with heteroatoms, by reaction with excess ammonia for from 12 to 36 hours in a solvent at 7.5 bar and reaction temperature of 135-180° C. is described. The nitrogen-containing acridinyl-based pincer complex carbonylchlorohydrido[4,5-(di-i-propylphosphinomethylacridino)ruthenium (II)] is used as catalyst and yields in the range from 78 to 96% are achieved.

In addition, WO 2010018570 describes the use of quinolinyl-based pincer ligands with comparable yields. However, the catalyst or ligand disclosed in these publications is stable to neither air nor moisture; the increased process outlay resulting therefrom does not allow an inexpensive process for preparing amines.

A synthesis of primary amines by ruthenium-catalysed amination of secondary alcohols using various ligands is described in the literature by Imm et al. (S. Imm, S. Bähn, L. Neubert, H. Neumann, M. Beller; Angew. Chem. 2010, 122, 8303-6). It was found there that high yields of the amination products can be obtained only when the ruthenium coordination compound used as catalyst comprises a complicated ligand comprising both phosphorus and nitrogen. The best results for the amination of cyclohexanol were obtained using the ligand CataCXium PCy (87% yield), while purely phosphorus-containing ligands allow a maximum yield of 20%. However, the yield which can be obtained when using CataCXium PCy is still too low for an economical process. Imm et al. found that xanthphos catalysts do not display any activity.

In the same way, Pingen et al. (D. Pingen, C. Müller, D. Vogt, Angew. Chem. 2010, 122, 1-5), show that although nitrogen-free phosphane ligands allow moderate to high selectivities to cyclohexylamines in the amination of cyclohexanol, these catalysts have only a low activity (maximum conversion=39%).

The direct single-stage liquid-phase amination of functionalized and/or polyhydric alcohols by means of ammonia has also been described over heterogeneous catalysts. In DE 3903367, the ether-diol diethylene glycol was aminated by means of liquid ammonia at 200° C. in a 30 bar hydrogen atmosphere over various zirconium dioxide-supported Cu—Co—Ni catalysts. However, in no case was the ether-diamine isolated as reaction product, but instead only the subsequent products aminoethoxyethanol and morpholine were isolated.

However, when using a Co—Cu—Zn catalyst, polyetheramines can, according to U.S. Pat. No. 4,153,581, be successively prepared even at 140° C., but the presence of hydrogen is said to be absolutely necessary. It is common to all further examples known in the literature of the heterogeneously or homogeneously catalysed amination of alcohols at moderate temperatures in the presence of hydrogen ((a) dodecyl alcohol in: H. Kimura, Y. Yokota, Y. Sawamoto, *Catal. Lett.* 2005, 99 (3-4), 133-140; (b) polyvinyl alcohol in: G. Vedage, M. Ford, J. Armor, *Catalysis of organic reactions* 2003, 89, 517-52) or absence of hydrogen ((a) 2,5-dimethoxybenzyl alcohol in: P. Likhar, R. Arundhathi, M. Kantam, P. Prathima, *Eur. J. Org. Chem.* 2009, 5383-59; (b) hexadecyl alcohol in: R. Pruett, M. Keenan, E. Mozelski, U.S. Pat. No. 5,103,058, 1992.) that only nucleophilic primary or secondary amines can be reacted with the optionally functionalized alcohol.

It is therefore not possible for a person skilled in the art to see that representatives of this class of substrates can be reacted with the significantly less nucleophilic ammonia in high yield to form the corresponding primary amines, especially since in this case a reaction of the primary amine formed with a yet unreacted alcohol occurs quite preferentially compared to the reaction of ammonia, which leads to formation of by-products.

In related heterogeneously catalysed processes, catalysts based on Co—Cr—Mn in the presence of $P_2O_5$ at 140-230° C. and a hydrogen pressure of 200-300 bar (DE 1543377), based on $Ni/Al_2O_3$ at 200-230° C. and a hydrogen pressure of 15-20 bar (RO 63243) or based on calcium silicoaluminates at 260-300° C. and a hydrogen pressure of 200 bar (DE 1278432) have also been described. Alcohols are aminated under comparable conditions by the processes described in DE 19859776 (180-230° C. over Cu—CuO/$TiO_2$), DE 102006061045 (180-250° C. over Ni—Cu/$ZrO_2$), DE 102006061042 (180-220° C. over Ni—Cu—Ru/$ZrO_2$), WO 2008072428 (180-250° C. over Ru/$ZrO_2$) and WO2007077903 (180-250° C. over Ru/$Al_2O_3$); however, a hydrogen atmosphere is likewise additionally required here.

The examples mentioned show, by way of example, the need for processes for achieving activation of alcohols, in particular relatively long-chain alcohols too, even without the use of hydrogen and realizing amination in high yields.

According to DE 1570542, polyether diols such as polypropylene glycol can be converted directly in high yields of up to 95.8% into the corresponding diamines when the reaction is carried out at 240° C. in the presence of Raney nickel catalysts. However, this procedure, too, is unsuitable for the reaction of thermolabile substrates. Such thermolabile substrates are, in particular, functionalized alcohols whose substituent patterns in the substrate or in the amine formed therefrom allow an intermolecular or intramolecular secondary or subsequent reaction which leads to degradation thereof or to formation of unreactive relatively high molecular weight (possibly polymeric) products.

The prior art indicted does not disclose any process which describes the direct single-stage, hydrogen-free liquid-phase amination of alcohols by means of ammonia to primary amines in high yields using a homogeneous catalyst system based on xantphos and a transition metal compound under mild reaction conditions and in the absence of hydrogen. On the contrary, the prevailing opinion in the literature is that such catalysts do not display reactivity in such amination reactions.

DESCRIPTION OF THE INVENTION

Surprisingly and contrary to current literature opinion (e.g. Imm et al., Pingen et al.), a process which allows the direct amination of alcohols by means of ammonia in high yields in the presence of a catalyst as described in Claim 1 and in the absence of hydrogen has now been found. The present invention therefore provides a process which allows the direct, homogeneously catalysed liquid-phase amination of alcohols, in particular by means of a superstoichiometric amount of ammonia based on hydroxyl groups to be aminated, preferably in the absence of hydrogen, using a catalyst system containing a transition metal compound and a xantphos ligand.

An advantage of the process of the invention is that the isolation and purification of intermediates, which is otherwise necessary in the reaction, is avoided.

Another advantage is that nitrogen-containing phosphane ligands, which are air-sensitive, can be dispensed with as ligands for the catalyst.

A further advantage is that nitrogen-free phosphane ligands which can be prepared simply and on a large scale can be employed.

Another advantage is that the use of problematical auxiliaries such as azides can be avoided.

An additional advantage is also that the formation of coproducts does not occur in the process of the invention and the formation of by-products can be reduced to a low level by appropriate selection of process conditions and catalyst.

A further advantage is that the alcohol is reacted in the dissolved state.

Another advantage is that the amination of the alcohol can be effected without isolation and/or purification of intermediates.

The process of the invention for preparing primary amines comprises the steps

A) provision of a solution of an alcohol in a fluid, nongaseous phase,
B) bringing the phase into contact with free ammonia and/or at least one ammonia-liberating compound and a homogeneous catalyst system comprising at least one xantphos ligand and a transition metal compound, and optionally
C) isolation of the primary amine formed in process step B).

For the purposes of the present invention, the term "primary amine" likewise encompasses salts thereof and mixtures of the amine and/or its salts.

For the purposes of the present invention, the term "alcohol" refers to an organic compound which has at least one hydroxyl group. In addition, the alcohol described in this way can bear one or more functional groups other than —OH in the molecule.

For the purposes of the present invention, the term "xantphos ligand" refers to a compound of the general formula 1, general formula 1

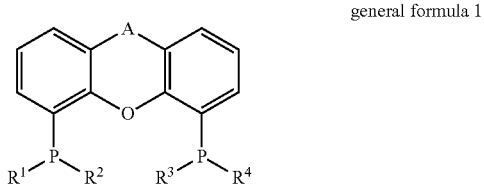

where $R^1$, $R^2$, $R^3$ and $R^4$ are identical or different and are selected independently from the group containing, preferably consisting of, phenyl, tert-butyl and isopropyl, and A is selected from the group containing, preferably consisting of, —C(CH$_3$)$_2$—, —CH$_2$CH$_2$—, —Si(CH$_3$)$_2$—, —S—, —O—, —C(C(CH$_3$)$_2$)— and

Preference is given to using xantphos ligands in which $R^1=R^2=R^3=R^4$ phenyl and A=—C(CH$_3$)$_2$—.

In a preferred alternative embodiment, xantphos ligands in which $R^1=R^2=R^3=R^4$=phenyl and A = 

are used.

The transition metal is preferably selected from the group containing, preferably consisting of, ruthenium, cobalt, rhodium, iridium, nickel, palladium and platinum and also the other platinum metals and iron. The transition metal is particularly preferably selected from the group consisting of ruthenium, iridium and palladium; particularly preferably from the group consisting of ruthenium and iridium, in particular ruthenium.

It may be pointed out that, depending on the selected combination of the above-described elements forming the catalyst, this can have an electric charge and be used in the form of a salt formed with appropriate counterions.

In a particularly preferred embodiment, the catalyst is the xanthene-based coordination compound carbonylchlorohydrido[9,9-dimethyl-4,5-bis(diphenylphosphino)xantheno]ruthenium(II):

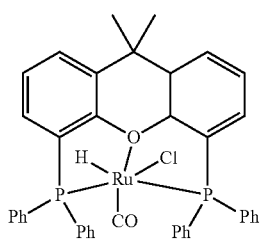

Carbonylchlorohydrido[9,9-dimethyl-4,5-bis(diphenylphosphino)xantheno]ruthenium(II)

The process of the invention can be utilized for the direct amination of primary or secondary alcohols by means of ammonia to primary amines. Alcohols which are preferably used in process step A) are characterized in that they cannot be vaporized without decomposition or can be vaporized to only an unsatisfactory extent and are therefore not suitable for a gas-phase reaction. Such alcohols are, for example, aliphatic or aromatic primary and secondary, optionally polyhydric alcohols (e.g. the propanols, butanols, pentanols, hexanols, octanols, nonanols, decanols or higher alcohols), optionally polyhydric benzyl alcohols, optionally polyhydric cycloaliphatic alcohols (e.g. cyclopentanol, cyclohexanol), or other optionally polyhydric hydroxy-functionalized organic compounds having a primary or secondary OH function, e.g. hydroxy-functionalized heterocyclic compounds.

Alcohols which are particularly preferably used in process step A) are selected from the group of aliphatic, linear ω-hydroxycarboxylic acids, in particular those having a carbon chain comprising at least 8 carbon atoms, for example 9-hydroxynonanoic acid, 11-hydroxyundecanoic acid, 12-hydroxydodecanoic acid and 15-hydroxypentadecanoic acid.

Further alcohols which are particularly preferably used in process step A) are, owing to the mild reaction conditions, selected from the group of relatively high molecular weight alcohols having a molecular weight of at least 100 g/mol, preferably at least 140 g/mol. Typical representatives of this group include, in particular, the sugar alcohols, for example isosorbitol, isomannitol and derivatives thereof selected from the group of ester and ether derivatives, glycosides, glycals, deoxy sugars and glycolipids, and polyols such as polyethylene glycols.

Examples of alcohol concentrations used in the process of the invention are in the range from 0.1 to 1000 mmol/l, preferably from 0.1 to 100 mmol/l and particularly preferably from 0.1 to 10 mmol/l.

The fluid phase used in process step A) can be formed by a solvent or a gas which is present in liquefied or supercritical form under the process conditions, in particular ammonia, or mixtures of the components mentioned.

In this context, water or organic solvents or mixtures thereof, with these mixtures being able to be a homogeneous solution or an emulsion, can be used as solvents. Particular preference is given to using at least one organic solvent. A nonlimiting selection of suitable organic solvents encompasses benzene, toluene, the xylene isomers, mesitylene, dioxane, THF, dimethoxyethane, anisole, cyclohexane, tert-butyl alcohol and tert-amyl alcohol.

For the purposes of the present invention, ammonia or an ammonia-liberating compound used in process step B) can also be, in particular, liquid or supercritical ammonia and/or a solution of ammonium salts in a solvent (e.g. including ammonium hydroxide in water).

Preference is given to using gaseous or liquefied ammonia as free ammonia in process step B).

The ammonia is used in process step B) in a molar ratio relative to the hydroxyl groups in the alcohol of, in particular, at least 5:1, preferably 50:1, particularly preferably 500:1.

In a preferred embodiment, process step B) is carried out under superatmospheric pressure. Illustrative pressures in the process of the invention are in the range from 1 to 1000 bar, preferably from 5 to 500 bar, particularly preferably from 5 to 100 bar and very particularly preferably from 5 to 20 bar. The pressure can be built up by injection of the ammonia and/or a further gas, in particular an inert gas such as nitrogen or argon, with pressure buildup by means of gas mixtures of the two being preferred.

The temperatures in process step B) which describe the process of the invention are in a range which keeps the decomposition reactions of alcohol, primary amine and all further intermediates occurring during the course of the process leading to formation of by-products as a result of thermal stress to a minimum. For example, the temperatures are in a range from 80 to 220° C., preferably from 100 to 200° C. and particularly preferably from 120 to 170° C., measured in the fluid phase.

A preferred embodiment of the process is characterized in that the volume ratio of the liquid phase to the gas phase in process step B is greater than or equal to 0.05, preferably greater than 0.1, in particular greater than 0.2.

Preference is given, according to the invention, to the process being carried out in the absence of hydrogen, where absence of hydrogen means that no hydrogen is additionally supplied to the reaction; any traces of hydrogen present in the air count as "in the absence of hydrogen" for the purposes of the present invention.

EXAMPLES

Example 1

Direct Single-Stage Amination of the Primary OH Group of Methyl 12-hydroxydodecanoate by Means of Ammonia over a Homogeneous, Nitrogen-Free Ru-Xanthenyl Catalyst, According to the Invention 0.23 g of methyl 12-hydroxydodecanoate (1 mmol), 0.057 g of carbonylchlorohydridotris(triphenylphosphane)ruthenium(II) as precursor compound, 0.035 g of 9,9-dimethyl-4,5-bis(diphenylphenylphosphino)xanthene as ligand and V (see Table 1) ml of 2-methyl-2-butanol were placed in a 50 ml high-pressure reactor and flushed with nitrogen in the closed and gastight reactor at room temperature. 1.5 ml of liquid ammonia were then introduced over a period of 0.15 minutes and the reaction mixture was heated to T° C. (see Table 1), with a pressure of up to 35 bar being established. After a reaction time of 20 hours, the reactor was cooled, depressurized, the reaction mixture was taken up in ethanol and filtered. According to the NMR analytical results shown in Table 1, the substrate can be successfully converted into the primary amine.

TABLE 1

| Input | V [ml]$^a$ | T [° C.]$^b$ | C [%]$^c$ | $A_{prim}$ [%]$^d$ | $A_{sec}$ [%]$^e$ |
|---|---|---|---|---|---|
| 1 | 1 | 110 | 45 | 20 | 5 |
| 2 | 1 | 130 | 100 | 30 | 5 |
| 3 | 3 | 130 | 100 | 55 | 8 |

$^a$Volume of 2-methyl-2-butanol;
$^b$Reaction temperature;
$^c$Conversion of the substrate;
$^d$Yield of the primary amine;
$^e$Yield of the secondary amine Example 2

Direct Single-Stage Amination of the Secondary Alcohol Isosorbide by Means of Ammonia over a Homogeneous, Nitrogen-Free Ru-Xanthenyl Catalyst, According to the Invention 0.146 g (1 mmol) of isosorbide, 0.057 g of (0.06 mmol) of carbonylchlorohydridotris(triphenylphosphane)ruthenium (II), 0.035 g (0.06 mmol) of 9,9-dimethyl-4,5-bis(diphenylphenylphosphino)xanthene and 1 ml of tert-amyl alcohol were placed in a 50 ml high-pressure reactor and flushed with nitrogen in the closed and gastight reactor at room temperature. 1.5 ml of liquid ammonia were then introduced over a period of 0.15 minutes and the reaction mixture was heated to 150° C., with a pressure of up to 35 bar being established. After a reaction time of 20 hours, the reactor was cooled, depressurized, the reaction mixture was taken up in ethanol and filtered. According to NMR analysis, the alcohol groups are reacted to an extent of 90% and the corresponding primary amino groups are obtained in a yield of 70%; no secondary amines were detected.

Example 3

Direct Single-Stage Amination of 2-Octanol by Means of Ammonia over a Homogeneous Ruthenium Catalyst Under an argon atmosphere, $m_o$ g of 2-octanol, $m_{Ru}$ g of [carbonylchlorohydridotris(triphenylphosphane)ruthenium (II)] as catalyst, $m_P$ g of 9,9-dimethyl-4,5-bis(diphenylphosphino)xanthene and $V_{solv}$ ml of 2-methyl-2-butanol as solvents were introduced into the glass liner of a 100 ml Hastelloy autoclave. The autoclave was closed, pressurized three times with 20 bar of argon and depressurized each time and once again pressurized with 15 or 30 bar of argon. $m_A$ g of liquid ammonia were then introduced into the autoclave. The reaction mixture was stirred at room temperature for 10 minutes (600 rpm), subsequently heated while stirring to an internal temperature of 170° C. and maintained at this temperature for 48 hours, with a pressure of p bar being established. After cooling to room temperature, careful depressurization of the mixture and pressurization with 20 bar of argon three times with subsequent depressurization each time, the autoclave was opened and the reaction mixture was analysed by means of a gas chromatograph. Reaction parameters and conversions and selectivities to the desired primary amine 2-octylamine are shown in Tab. 2. The results show that the selectivity to the target product can be increased both by increasing the $V_{liq}/_{gas}$ ratio and by increasing the pressure and also by simultaneously increasing both parameters.

TABLE 2

| No. | $m_O$ [g][1] | $m_{Ru}$ [g][2] | $m_P$ [g][3] | $V_{solv}$ [ml][4] | $m_A$ [g][5] | p [bar][6] | $V_{liq}/V_{gas}$ [—][7] | C [%][8] | S [%][9] |
|---|---|---|---|---|---|---|---|---|---|
| 3.1 | 2.6 | 0.58 | 0.35 | 20 | 6.0 | 54 | 1.14 | 99 | 89 |
| 3.2 | 2.6 | 0.58 | 0.5 | 20 | 6.0 | 89 | 1.14 | 99 | 98 |

[1]Mass of 2-octanol;

[2]mass of [carbonylchlorohydridotris(triphenylphosphane)ruthenium(II)];

[3]mass of xantphos;

[4]volume of solvent;

[5]mass of ammonia;

[6]pressure established under the reaction conditions;

[7]ratio of the liquid phase volume to the gas phase volume;

[8]conversion of 2-octanol;

[9]selectivity to 2-octylamine.

Example 4

Direct Single-Stage Amination of 1-Hexanol by Means of Ammonia over a Homogeneous Ruthenium Catalyst Under an argon atmosphere, $m_H$ g of 1-hexanol, $m_{Ru}$ g of [carbonylchlorohydridotris(triphenylphosphane)ruthenium (II)] and $m_P$ g of 9,9-dimethyl-4,5-bis(diphenylphosphino) xanthene as catalyst and $V_{solv}$ ml of 2-methyl-2-butanol as solvent were introduced into a 50 ml steel tube. The vessel was closed, pressurized three times with 20 bar of argon and depressurized each time. The vessel was then cooled by means of dry ice and $m_A$ g of ammonia were condensed in. After pressurization to a differential pressure of a further p bar of argon, the reactor was heated to 130° C. and maintained at this temperature for 20 hours. After cooling to room temperature, the reactor was depressurized and opened, the solvent was removed on a rotary evaporator and the residue was dissolved in methanol and then analysed by gas chromatography. Reaction parameters and conversions and selectivities to the desired reaction product 1-hexylamine are shown in Tab. 3. The results show that the selectivity to the target product can be increased both by increasing the $V_{liq}/V_{gas}$ ratio and by increasing the pressure and by simultaneously increasing both parameters.

Example 5

Direct Single-Stage Amination of Methyl 12-Hydroxydodecanoate (Hydroxy Acid) by Means of Ammonia over a Homogeneous Ruthenium Catalyst Under an argon atmosphere, $m_H$ g of methyl 12-hydroxydodecanoate, $m_{Ru}$ g of [carbonylchlorohydridotris(triphenylphosphane)ruthenium(II)] and $m_P$ g of 9,9-dimethyl-4,5-bis(diphenylphosphino)xanthene as catalyst and $V_{solv}$ ml of 2-methyl-2-butanol as solvent were introduced into a 50 ml steel tube. The vessel was closed, pressurized with 20 bar of argon three times and depressurized each time. The vessel was then cooled by means of dry ice and $m_A$ g of ammonia were condensed in. After pressurization to a differential pressure of a further p bar of argon, the reactor was heated to 130° C. and maintained at this temperature for 20 hours. After cooling to room temperature, the reactor was depressurized and opened, the solvent was removed on a rotary evaporator and the residue was dissolved in methanol and then analysed by gas chromatography. Reaction parameters and conversions and selectivities to the desired reaction product 1-hexylamine are shown in Tab. 4. The results show that the selectivity to the target product can be increased both by increasing the $V_{liq}/V_{gas}$ ratio and by increasing the pressure and by simultaneously increasing both parameters.

TABLE 3

| No. | $m_H$ [g][1] | $m_{Ru}$ [g][2] | $m_P$ [g][3] | $V_{solv}$ [ml][4] | $m_A$ [g][5] | p [bar][6] | $V_{liq}/V_{gas}$ [—][7] | C [%][8] | S [%][9] |
|---|---|---|---|---|---|---|---|---|---|
| 4.1 | 0.10 | 0.029 | 0.017 | 1 | 0.3 | 0 | 0.03 | 100 | 31 |
| 4.2 | 0.10 | 0.029 | 0.017 | 1 | 0.3 | 20 | 0.03 | 100 | 37 |
| 4.3 | 0.41 | 0.116 | 0.069 | 4 | 1.2 | 0 | 0.14 | 80 | 50 |
| 4.4 | 0.41 | 0.116 | 0.069 | 4 | 1.2 | 20 | 0.14 | 65 | 48 |

[1]Mass of 1-hexanol;

[2]mass of [carbonylchlorohydridotris(triphenylphosphane)ruthenium(II)];

[3]mass of xantphos;

[4]volume of solvent;

[5]mass of ammonia;

[6]pressure established under the reaction conditions;

[7]ratio of the liquid phase volume to the gas phase volume;

[8]conversion of 1-hexanol;

[9]selectivity to 1-hexylamine.

TABLE 4

| No. | $m_H$ [g][1] | $m_{Ru}$ [g][2] | $m_P$ [g][3] | $V_{solv}$ [ml][4] | $m_A$ [g][5] | p [bar][6] | $V_{liq}/V_{gas}$ [—][7] | C [%][8] | S [%][9] |
|---|---|---|---|---|---|---|---|---|---|
| 5.1 | 0.23 | 0.029 | 0.017 | 1 | 0.3 | 0 | 0.04 | 100 | 30 |
| 5.2 | 0.23 | 0.029 | 0.017 | 1 | 0.3 | 20 | 0.04 | 98 | 42 |
| 5.3 | 0.92 | 0.116 | 0.069 | 4 | 1.2 | 0 | 0.16 | 96 | 50 |
| 5.4 | 0.92 | 0.116 | 0.069 | 4 | 1.2 | 20 | 0.16 | 77 | 61 |

[1]Mass of methyl 12-hydroxydodecanoate;
[2]mass of [carbonylchlorohydridotris(triphenylphosphane)ruthenium(II)];
[3]mass of xantphos;
[4]volume of solvent;
[5]mass of ammonia;
[6]pressure established under the reaction conditions;
[7]ratio of the liquid phase volume to the gas phase volume;
[8]conversion of methyl 12-hydroxydodecanoate;
[9]selectivity to methyl 12-aminododecanoate.

Example 6

Direct Single-Stage Amination of Alcohols and Hydroxy Acids by Means of Ammonia Over a Homogeneous Ruthenium Catalyst and Xantphos at a high $V_{liq}/V_{gas}$ (According to the Invention)

Under an argon atmosphere, $m_E$ g of starting material, $m_{Ru}$ g of [carbonylchlorohydridotris(triphenylphosphane)ruthenium(II)] and $m_P$ g of 9,9-dimethyl-4,5-bis(diphenylphosphino)xanthene as catalyst and $V_{solv}$ ml of 2-methyl-2-butanol as solvent were introduced into a 50 ml steel tube. The vessel was closed, pressurized three times with 20 bar of argon and depressurized each time. The vessel was then cooled by means of dry ice and $m_A$ g of ammonia were condensed in. The reactor is heated to T° C. and maintained at this temperature for 20 hours. After cooling to room temperature, the reactor was depressurized and opened, the solvent was removed on a rotary evaporator and the residue was dissolved in methanol and then analysed by gas chromatography. Reaction parameters and conversions and selectivities to the desired reaction product are shown in Tab. 5. The results show that many different hydroxy-functionalized substrates can be aminated by the method described.

TABLE 5

| Starting material | $m_E$ [g][1] | $m_{Ru}$ [g][2] | $m_P$ [g][3] | $V_{solv}$ [ml][4] | $m_A$ [g][5] | T [° C.][6] | $V_{liq}/V_{gas}$ [—][7] | C [%][8] | S [%][9] |
|---|---|---|---|---|---|---|---|---|---|
| Tetraethylene glycol | 0.19 | 0.029 | 0.017 | 1 | 1 | 140 | 0.06 | 100 | 97 |
| p-Hydroxymethylbenzyl alcohol | 0.14 | 0.029 | 0.017 | 3 | 1 | 150 | 0.10 | 100 | 48 |
| p-Hydroxymethylbenzyl alcohol | 0.14 | 0.029 | 0.017 | 5 | 1 | 150 | 0.15 | 100 | 76 |
| m-Hydroxymethylbenzyl alcohol | 0.14 | 0.029 | 0.017 | 5 | 1 | 150 | 0.15 | 100 | 70 |
| 1-Octanol | 0.13 | 0.029 | 0.017 | 1 | 1 | 130 | 0.06 | 99 | 53 |
| 1-Octanol | 0.13 | 0.029 | 0.017 | 3 | 1 | 130 | 0.10 | 80 | 79 |
| 1-Octanol | 0.13 | 0.029 | 0.017 | 3 | 1 | 140 | 0.10 | 99 | 80 |
| 2-Phenylethanol | 0.12 | 0.029 | 0.017 | 3 | 1 | 140 | 0.10 | 99 | 94 |
| Benzyl alcohol | 0.11 | 0.029 | 0.017 | 3 | 1 | 140 | 0.10 | 100 | 87 |
| 3-Pyridinylmethanol | 0.11 | 0.029 | 0.017 | 3 | 1 | 140 | 0.10 | 100 | 96 |
| Methyl 10-hydroxydecanoate | 0.20 | 0.029 | 0.017 | 3 | 1 | 130 | 0.10 | 100 | 75 |
| Methyl 4-hydroxymethylbenzoate | 0.17 | 0.029 | 0.017 | 3 | 0.6 | 130 | 0.09 | 100 | 92 |
| Isosorbide | 0.15 | 0.058 | 0.035 | 1 | 0.6 | 150 | 0.04 | 90 | 22 |
| Isosorbide | 0.15 | 0.058 | 0.035 | 1 | 0.6 | 170 | 0.04 | 100 | 96 |
| 1,4-Cyclohexanediol | 0.11 | 0.029 | 0.017 | 1 | 1 | 140 | 0.06 | 95 | 75 |
| 4,4'-Isopropylidenedicyclohexanol | 0.24 | 0.029 | 0.017 | 1 | 1 | 150 | 0.06 | 99 | 97 |
| Ethyl 4-hydroxycyclohexanecarboxylate | 0.18 | 0.029 | 0.017 | 2 | 0.6 | 130 | 0.06 | 82 | 95 |
| 2-Adamantanol | 0.15 | 0.058 | 0.035 | 1 | 0.6 | 150 | 0.06 | 99 | 98 |

[1]Mass of methyl 12-hydroxydodecanoate;
[2]mass of [carbonylchlorohydridotris(triphenylphosphane)ruthenium(II)];
[3]mass of xantphos;
[4]volume of solvent;
[5]mass of ammonia;
[6]reaction temperature;
[7]ratio of the liquid phase volume to the gas phase volume;
[8]conversion of methyl 12-hydroxydodecanoate;
[9]selectivity to methyl 12-aminododecanoate

The invention claimed is:

1. A process for preparing a primary amine, comprising:
contacting a solution of an alcohol in a fluid, nongaseous phase,
with free ammonia, an ammonia-liberating compound, or both, and a homogeneous catalyst system comprising carbonylchlorohydrido[9,9-dimethyl-4,5-bis(diphenylphosphino)xantheno]ruthenium(II)] as a xantphos ligand; and optionally isolating the primary amine obtained in the contacting.

2. The process according to claim 1,
wherein the alcohol is an aliphatic, linear ω-hydroxycarboxylic acid having a carbon chain comprising at least 8 carbon atoms.

3. The process according to claim 1,
wherein the alcohol has a concentration of from 0.1 to 1000 mmol/l, based on the fluid phase.

4. The process according claim 1,
wherein the contacting comprises contacting with liquid or supercritical ammonia, with a solution of ammonium salts in a solvent, or both.

5. The process according to claim 1,
wherein in the contacting, the ammonia has a molar ratio to hydroxyl groups in the alcohol of at least 5:1.

6. The process according to claim 1,
wherein the contacting is carried out at a pressure of from 1 to 1000 bar.

7. The process according to claim 1,
wherein the contacting is carried out in a temperature range of from 80 to 220° C.

8. The process according claim 1,
wherein a volume ratio of a liquid phase to a gas phase in the contacting is at least 0.05.

9. The process according to claim 1,
wherein the process is carried out in the absence of hydrogen.

10. The process according to claim 1, wherein the alcohol has a concentration of from 0.1 to 100 mmol/l based on the fluid phase.

11. The process according to claim 1, wherein the alcohol has a concentration of from 0.1 to 10 mmol/l based on the fluid phase.

12. The process according to claim 1, wherein in the contacting, the ammonia has a molar ratio to hydroxyl groups in the alcohol of at least 50:1.

13. The process according to claim 1, wherein in the contacting, the ammonia has a molar ratio to hydroxyl groups in the alcohol of at least 500:1.

14. The process according to claim 1, wherein the contacting is carried out at a pressure of from 5 to 500 bar.

15. The process according to claim 1, wherein the contacting is carried out at a pressure of from 5 to 20 bar.

16. The process according to claim 1, wherein the contacting is carried out in a temperature range of from 100 to 200° C.

17. The process according to claim 1, wherein the contacting is carried out in a temperature range of from 120 to 170° C.

18. The process according to claim 1, wherein a volume ratio of a liquid phase to a gas phase in the contacting is greater than or equal to 0.1.

* * * * *